United States Patent
Burns et al.

(10) Patent No.: US 6,508,767 B2
(45) Date of Patent: Jan. 21, 2003

(54) ULTRASONIC HARMONIC IMAGE SEGMENTATION

(75) Inventors: Peter N. Burns, Toronto (CA); David Hope Simpson, Kenmore, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/782,237

(22) Filed: Feb. 12, 2001

(65) Prior Publication Data

US 2001/0039381 A1 Nov. 8, 2001

Related U.S. Application Data

(60) Provisional application No. 60/182,940, filed on Feb. 16, 2000.

(51) Int. Cl.[7] .................................................. A61B 8/00
(52) U.S. Cl. ........................ 600/443; 600/454; 600/455
(58) Field of Search .............................. 600/453, 458, 600/455, 454, 456, 443, 447

(56) References Cited

U.S. PATENT DOCUMENTS

| 5,526,816 A | | 6/1996 | Arditi |
| 6,095,980 A | * | 8/2000 | Burns et al. ............... 600/453 |
| 6,132,377 A | | 10/2000 | Bolorforosh et al. |
| 6,155,981 A | | 12/2000 | Ermert et al. |
| 6,186,950 B1 | * | 2/2001 | Averkiou et al. ........... 600/440 |
| 6,190,322 B1 | * | 2/2001 | Clark .......................... 600/443 |
| 6,213,951 B1 | * | 4/2001 | Krishnan et al. ........... 600/458 |

* cited by examiner

Primary Examiner—Francis J. Jaworski
Assistant Examiner—Maulin Patel
(74) Attorney, Agent, or Firm—W. Brinton Yorks, Jr.

(57) ABSTRACT

An ultrasonic diagnostic imaging apparatus and method are provided for segmenting signals from nonlinear targets such as microbubble contrast agents. Received echo signals are separated into their constituent linear and nonlinear components by a Doppler filter using pulse inversion separation. A threshold level is derived from an estimate made of the contributions to the echo signal from linear scattering and noise. Echo signals which exceed the threshold level are segmented as nonlinear (microbubble-originating) signals and displayed as such, whereas signals not exceeding the threshold are suppressed in the image display.

38 Claims, 6 Drawing Sheets

ULTRASONIC HARMONIC IMAGE SEGMENTATION

This application claims the benefit of U.S. Provisional Application No. 60/182,940 filed Feb. 16, 2000.

This invention relates to ultrasonic diagnostic imaging and, in particular, to the segmentation (identification) of ultrasonic signals relating to tissue and ultrasonic contrast agents.

Ultrasonic contrast agents are in widespread use for the detection and diagnosis of disease. The current generation of ultrasonic contrast agents are comprised of tiny microbubbles, frequently encapsulated in soluble substances such as lipids, which are infused into a patient's bloodstream. These contrast agents have the property that, when insonified by an appropriate level of ultrasonic energy, the microbubbles will respond nonlinearly and return echo signals which contain nonlinear components of the linear transmit wave. These nonlinear components manifest themselves most strongly at harmonic multiples of the transmit frequency and hence the agents are generally referred to as harmonic contrast agents. Harmonic contrast agents advantageously provide excellent segmentation in relation to other echo signals because of their strong manifestation at the harmonic frequencies.

Since harmonic contrast agents travel through the cardiovascular system they are ideal for improving the diagnosis of blood flow and perfusion. Harmonic contrast agents are used to diagnose obstructions in the coronary arteries as described in U.S. patent application Ser. No. 09/645,872 or to diagnose myocardial perfusion as described in U.S. Pat. No. 5,833,613. The tiny microbubbles afford excellent patient safety for, unlike the problems that can result from large air emboli, the microbubbles are filtered from the bloodstream by normal bodily functions. A consequence of this is that the contrast agents, once infused into the body, do not remain there indefinitely but are rapidly removed. Hence it is necessary to perform contrast exams efficiently and expeditiously while the agent is in the bloodstream. It is a general practice prior to the introduction of the agent for the examining clinician to image the organ or region of the body which is the subject of the exam, to find the best acoustic window, probe inclination, and image planes by which the most diagnostic images can be acquired. Once the clinician has acquired these "baseline" images and formulated the specific technique for acquiring the images, the agent is infused and the desired contrast images quickly and efficiently acquired.

These baseline images, acquired as they are before any contrast agent has been introduced into the patient's bloodstream, should be free of any appearance of the agent. For instance, the contrast agent will often be displayed in color in the image, with the other structures in the body depicted in grayscale. In such a procedure the baseline images should appear free of any color in the images. But often these baseline images will be contaminated by artifacts resulting from noise, probe motion, or other sources. The clinician's natural response to seeing these artifacts is to turn down the transmit power or the receiver gain or to increase the noise rejection threshold in the images until these artifacts disappear. This, however, can reduce the sensitivity of the ultrasound system to contrast agents and thus degrade the diagnostic capability of the exam. It is desirable to minimize these artifacts in the image so that highly sensitive contrast images may be acquired without contamination by artifacts appearing to be contrast.

In accordance with the principles of the present invention an apparatus and method are provided for segmenting ultrasonic contrast image signals, thereby enabling the production of more sensitive and artifact-free ultrasonic harmonic images. Ultrasonic energy is transmitted and acquired so that nonlinear signals may be separated by the pulse inversion process. The received signal spectrum is analyzed to measure the relative power of linear and nonlinear components of the echo signal. The distribution of the received signal power and the ultrasound system noise threshold or sensitivity level are combined to produce a threshold against which the nonlinear signal level is compared. Signals that exceed the threshold are displayed in the nonlinear signal display format, and signals that are below the threshold are displayed in the linear signal format. Alternatively, signals falling below the threshold may not be displayed at all. This segmentation reduces the artifact level in both harmonic contrast and tissue harmonic images. The present invention also makes possible the display of a nonlinear signal which has been compensated for the effects of linear or weakly nonlinear tissue clutter and electronic noise.

Figure 1:
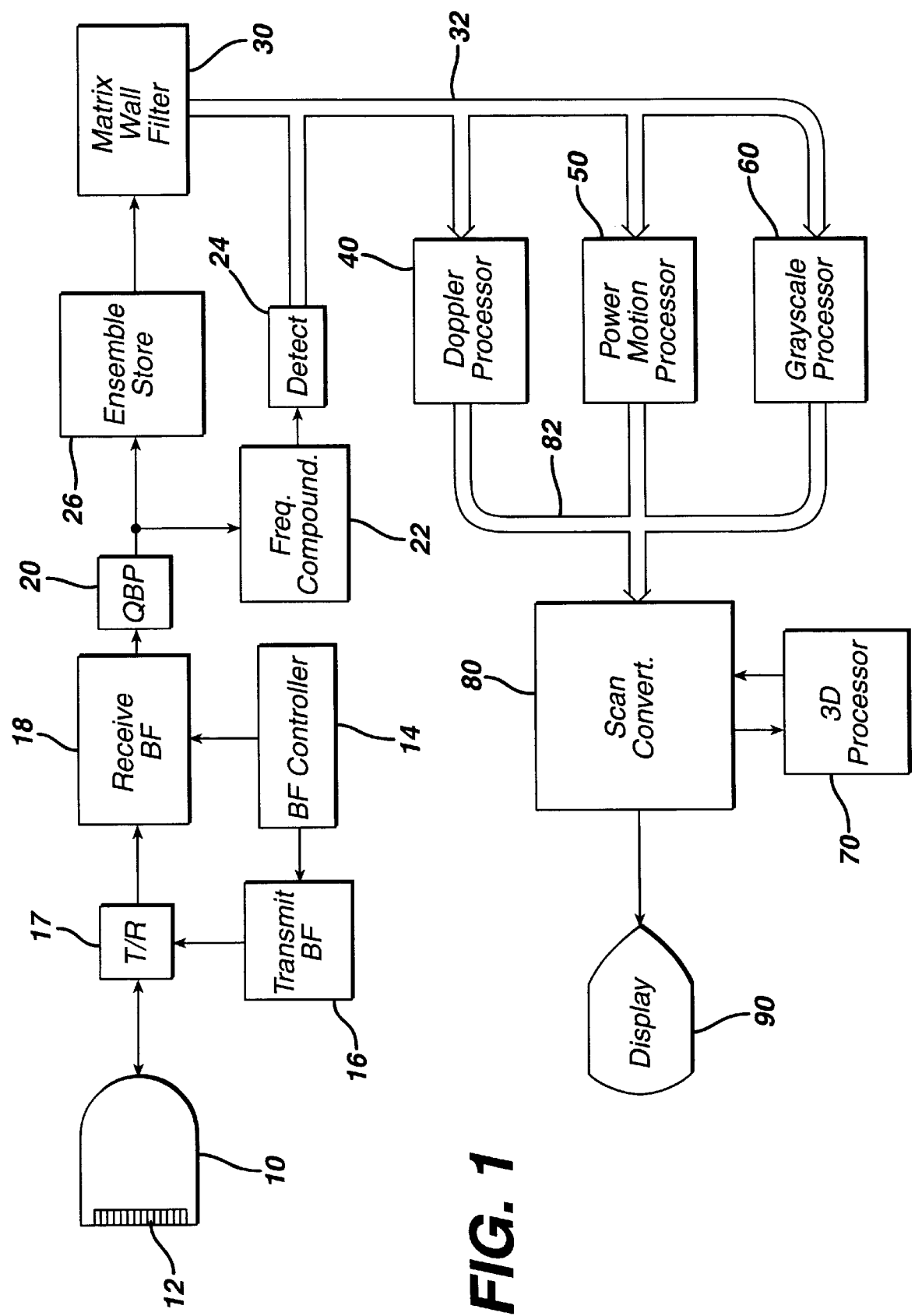
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A probe 10 which includes an array transducer 12 transmits ultrasonic energy into the body and receives echoes returned from tissue, cells and flowing substances in the body, including ultrasonic contrast agents when used. The array transducer can be a linear or curved array, and can be operated as a phased array or linear array. The transducer can also be any pulsed ultrasound transducer including a two-dimensional array transducer or even a single crystal transducer. Phased array operation is often preferred for Doppler studies. The timing of transmission and reception by the array transducer is synchronized by a beamformer controller 14 which is connected to a transmit beamformer 16 and a receive beamformer 18. The channels of each beamformer are connected to the individual elements of the array transducer so as to separately control the transmission and reception of signals from the individual elements. The transmit beamformer 16, under control of the beamformer controller, determines the time at which each element in the array is actuated to transmit a wave or pulse. This controlled timing of transmission enables the wave transmitted by the entire array to be steered in a given direction, that is, along a predetermined scanline, and to be focused at the desired depth of focus. The channels of the two beamformers are coupled to elements of the array by transmit/receive switches 17 which protect the receive beamformer channel inputs from high transmit voltages.

The echoes received by individual transducer elements are coupled to individual channels of the receive beamformer 18 by the transmit/receive switches 17. These input paths may also include preamplifiers to amplify the received echo signals and time gain compensation circuits to offset the effects of depth dependent attenuation. When the receive beamformer 18 is a digital beamformer as it is in the preferred embodiment, each channel of the beamformer is preceded by or includes an analog to digital converter. The channels of the beamformer continuously appropriately delay the echoes received by each transducer element from along the scanline so that the signals received from common points (sample volumes) along the scanline are brought into time coincidence. The continual delay variation effects dynamic focusing of the received echo signals along the scanline. The signals at the outputs of the channels are then combined to form a sequence of coherent echo signals.

Receive beamformers also conventionally perform other processing operations such as normalization of signal amplitudes to offset the effects of dynamic aperture changes. The receive beamformer may also be partitioned into two or more groups of channels, each with its own unique delay programming from the beamformer controller, to perform multiline reception. In multiline reception, each group of channels steers and focuses a received beam along its own scanline, thereby forming two or more received scanlines simultaneously. While multiline reception can increase frame rate by acquiring all of the scanlines of one image in less time, it is prone to aberration effects, since not all of the received scanlines are symmetrically coincident with the transmit aperture.

The sequence of coherent echoes received along the scanline can now be detected, scaled to a range of grayscale values, scanconverted to the desired image format, and displayed, thus forming a B mode image. In the apparatus of FIG. 1, the coherent echoes are demodulated by a quadrature bandpass (QBP) filter 20 into inphase (I) and quadrature (Q) samples. The I,Q samples can be Doppler processed to determine Doppler power, velocity, acceleration, variance, and the direction of flow or motion, and can also be used to detect the amplitude of the echo signal by the algorithm $(I^2+Q^2)^{1/2}$. In the embodiment of FIG. 1, the I,Q samples are processed to remove speckle by frequency compounding circuit 22. The echo amplitude is detected by a detector 24 and the detected echo signals are applied to a grayscale processor 60 by way of an echo data bus 32, where the echoes undergo log compression and are grayscale mapped. Details of a preferred technique for log compression and grayscale processing are found in U.S. Pat. No. 5,993,392. The grayscale signals are coupled to a scan converter 80 by way of an image data bus 82, where the R-θ scanline data is converted to the desired display format. The scan converted image is displayed on a display 90.

A detailed description of the QBP filter 20, the frequency compounding circuit 22, and the detector 24 may be found in U.S. Pat. No. 6,050,942.

For Doppler imaging the scanline is repetitively scanned over an interval of time to gather a sequence of temporal echoes at each sample volume along the scanline. This temporal echo sequence, called an ensemble, is acquired by a sequence of transmit waves, the repetition frequency of which is called the pulse repetition frequency, or PRF. Each individually transmitted wave or pulse exhibits a nominal frequency called the Doppler frequency which is in the normal r.f. range of diagnostic ultrasound. PRFs are usually in the kilohertz range or lower. The echo ensembles are accumulated in an ensemble store 26 from which completed ensembles are produced for Doppler processing.

The conventional first step in Doppler processing is wall filtering. When imaging or measuring bloodflow in the heart and blood vessels, the relatively low level echoes from blood cells can be overwhelmed by strong echoes reflected by nearby tissue such as a vessel or heart wall. Since the intent of the procedure is to image or measure bloodflow, the tissue echoes are, in this instance, clutter which can be eliminated. The circuitry which eliminates these unwanted signals is called a wall filter, since its basic purpose is to eliminate echoes from the heart and vessel walls. These signals may be discriminated by amplitude, frequency, or a combination of these two characteristics since tissue signals are generally of greater amplitude and lower frequency than bloodflow signals. A preferred technique for eliminating tissue signals as well as Doppler artifacts known as "flash" is shown in U.S. Pat. No. 5,197,477.

The wall filter may also be operated with a reverse characteristic so as to pass tissue Doppler signals to the exclusion of bloodflow Doppler signals. When these signals of the tissue are Doppler processed, images of moving tissue such as the heart muscle and valves can be produced. This imaging technique is known as tissue Doppler imaging.

The filtered Doppler signals, bloodflow or tissue, are applied to a Doppler processor 40 where they are used to perform Doppler estimation of the Doppler phase shift or signal intensity (power Doppler). Conventionally this is done by Fourier transform or autocorrelation of the Doppler signal data. A preferred technique is to perform a two dimensional autocorrelation which simultaneously estimates the Doppler phase shift and the reference or center frequency of the Doppler signal. The latter is useful for correction of the effects of depth dependent frequency attenuation in the phase shift estimation. Such a two dimensional Doppler processor is described in U.S. Pat. No. 5,386,830. Since the Doppler frequency or phase shift is proportional to the velocity of the bloodflow or tissue which returned the echoes, the production of a velocity, acceleration or variance number is straightforward. In colorflow Doppler the velocities of bloodflow are mapped to a color scale, coupled to the scan converter 80 over the image data bus 82, and overlaid on a grayscale image of the tissue structure containing the bloodflow. In power Doppler imaging the intensity of the Doppler signals is similarly mapped and displayed on a grayscale image. A power motion processor 50 is provided which develops images of moving structure from consecutive pulses as described in U.S. Pat. No. 5,718,229. Doppler, power motion, and grayscale image data can also be processed by 3D processor 70 to form three dimensional image presentations of the bloodflow and/or tissue, as described in U.S. Pat. Nos. 5,474,073 and 5,720,291.

Further details of the construction of the ultrasound system of FIG. 1 are more fully described in our U.S. Pat. No. 6,095,980, the contents of which are incorporated herein by reference. As we describe in that patent, the ultrasound system of FIG. 1 can be advantageously used to perform pulse inversion Doppler imaging. In the practice of pulse inversion Doppler, a sequence of ultrasound pulses of alternating phase, polarity, or amplitude is transmitted into the body. Alternating polarity introduces a phase shift of 180 degrees (π radians) between successive transmitted pulses. After filtering and demodulation, successive echoes signals are sampled at a constant delay, corresponding to a fixed location or "sample volume" in the body, to form a sampled Doppler signal. This Doppler signal may then be processed to estimate the spectrum of phase shifts between successive echoes. Equivalently, these phase shifts may be converted to Doppler shift frequencies by dividing the phase shift angle by the pulse repetition frequency (PRF). With pulse inversion Doppler, echoes due to linear and nonlinear scattering generate distinct phase shifts according to the degree of motion and nonlinear scattering present. Phase shifts from linear scattering are motion-shifted about 180 degrees, while those from even order nonlinear scattering are motion-shifted about 0 degrees. For contrast imaging at low intensities (low mechanical index MI), Doppler lowpass filters are used to isolate the nonlinear echoes from contrast microbubbles and suppress the linear echoes from tissue. The power of the filtered Doppler signal from each point in the scan plane is then approximately proportional to the local microbubble concentration. See Frush et al. in *Ultrasound in Medicine and Biology,* 21(1), at pp 41–47 (1995). Doppler power can be processed, thus, to generate a microbubble-specific image in which the signals from surrounding and underlying tissue are largely suppressed.

Because it is often desirable to see the underlying tissue, the Doppler power image is usually displayed as a colour overlay on top of a gray-scale tissue image. Segmentation techniques are required, therefore, to determine whether echoes from a given sample volume arise from microbubbles and should be displayed in colour, or whether the echoes arise from tissue and the gray-scale information should be displayed.

In the simplest method of segmentation for pulse inversion Doppler contrast imaging, a power threshold is set. Regions where the filtered Doppler signals are greater than the power threshold are interpreted as containing microbubbles and Doppler data are displayed as colour, while those regions with signals below the threshold are interpreted as tissue and grayscale data are displayed instead. When the Doppler frequency filters used in pulse inversion imaging are adequate to suppress linear echoes from tissue to a level below the electronic noise, then Doppler power-based segmentation performs well. With many practical pulse inversion Doppler filters, however, the linear echoes from highly echogenic moving structures such as the mitral valve leaflets and the endocardial border are not suppressed completely. Residual echo signals from linear scattering that are above the threshold are interpreted as arising from microbubbles and are displayed in colour, producing an artifact in the Doppler image. To suppress such artifacts, clinicians may increase the Doppler threshold (or, equivalently, decrease system gain), reducing the sensitivity to contrast microbubbles in the process.

Figure 2:
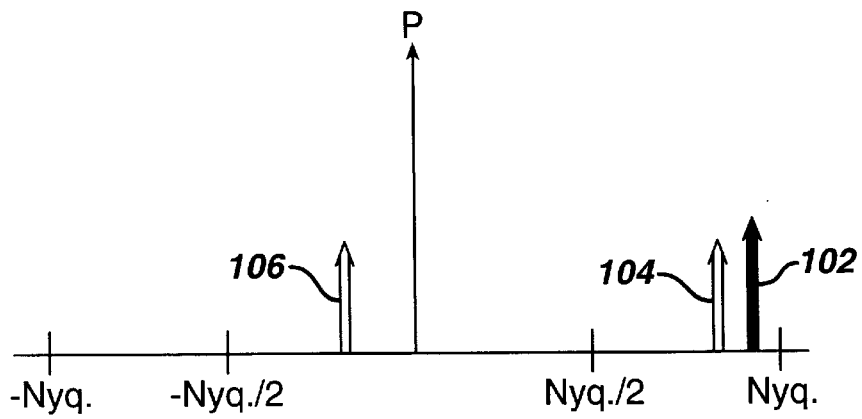
FIG. 2 illustrates a Doppler spectrum of tissue and contrast agent signal components.
Figure 3:
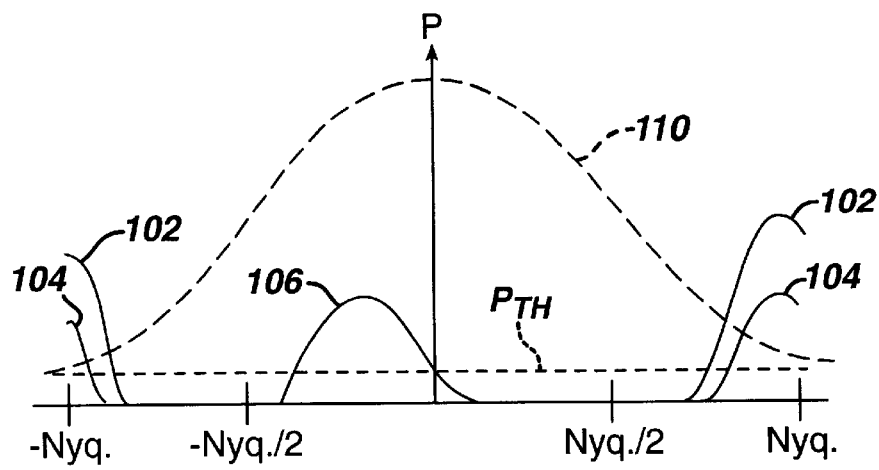
FIG. 3 illustrates a filter passband for separating the nonlinear components of the spectrum of FIG. 2.

This problem is illustrated by the spectral drawings of FIGS. 2 and 3. In these drawings as well as FIG. 4, the Doppler spectrum is shown extending from the (+)Nyquist limit on the right to −Nyquist on the left. The Nyquist limit for Doppler information is determined by the pulse rate frequency (PRF), the rate at which moving substances in the body are interrogated. Also shown in FIG. 2 are two half-Nyquist reference points at −Nyquist/2 and (+)Nyquist/2. As explained in our aforementioned patent, this spectral representation locates nonlinear signal components from stationary objects in the center of the spectrum and linear signal components from stationary objects at the ends (Nyquist limits) of the spectrum.

The spectrum in FIG. 2 is seen to contain three spectral components. Component 102 represents linear signal information received from nearly-stationary structure such as tissue. The component 104 represents linear signal information received from a slowly moving microbubble, and the component 106 represents nonlinear signal information received from the slowly moving microbubble.

To produce a pulse inversion Doppler contrast image of the microbubble contrast agent it is desirable to eliminate the linear echo components 102 and 104 from the tissue and the contrast agent. This could conveniently be done by a bandpass filter which passes the nonlinear signal components 106 in the center of the band while sharply cutting off any signals above and below the half-Nyquist points on the spectrum. However, given the limited number of signal samples which are usually available and the lengths of practical filters, such sharp filter cutoffs are usually not available. Rather, the filter characteristic will often appear with gradual rolloff as shown by filter characteristic 110 in FIG. 3, shown with typical spectral bands of the linear and nonlinear components 102, 104, and 106. As this drawing shows, even when a nominal power threshold $P_{TH}$ is imposed, residual linear echo signal components above the threshold will still be passed by the filter characteristic 110, a situation which is exacerbated by the fact that fundamental frequency components are nominally many dB above the second and higher order harmonics of the echo signal.

Figure 4:
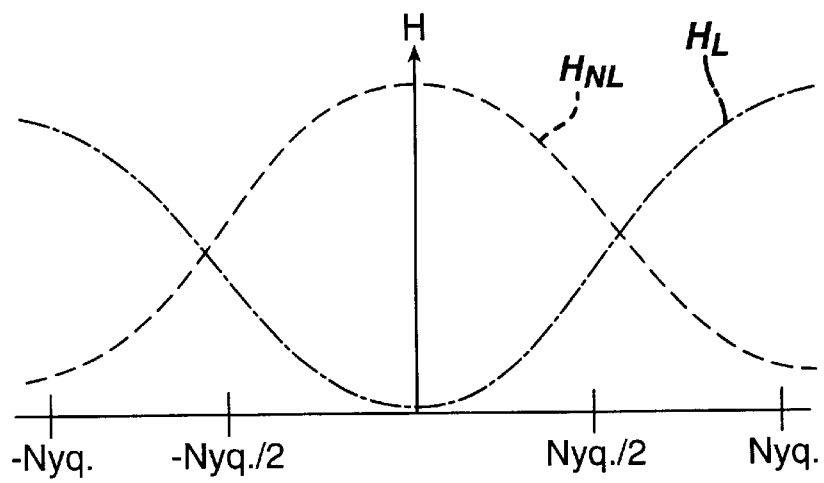
FIG. 4 illustrates filter characteristics for separating the linear and nonlinear components of the Doppler spectrum of FIGS. 2 and 3.

In accordance with the principles of the present invention a technique for segmenting pulse inversion Doppler image signals is provided which uses separate estimates of the intensities of both the nonlinear and the linear components of the echo signal. One embodiment of the inventive technique uses the power $P_L$ from filtered linear echo signals to estimate the power of the tissue signals in the filtered nonlinear signal power $P_{NL}$. Referring to FIG. 4, two filter passbands $H_{NL}$ and $H_L$ are shown. The passband $H_{NL}$ is centered around the nonlinear (even harmonic) center of the Doppler spectrum so as to preferentially pass nonlinear signal components. The passband $H_L$ is the complement of this, and is centered around the linear (odd harmonic) extremes of the Doppler spectrum so as to preferentially pass linear signal components. Thus, this embodiment filters the received echo signals with two filter characteristics, one for predominantly linear signal components (e.g., a highpass filter) and another for predominantly nonlinear signal components (e.g., a lowpass filter).

The effect of these filters is as follows. At low incident sound intensities, nonlinear propagation effects are weak and tissue will produce predominantly linear echo components, with total linear power, $T_l$. Microbubbles will produce significant linear and nonlinear echo components, with total powers denoted $B_l$ and $B_{nl}$ respectively. Agent and tissue echoes are assumed to have phase shifts $\phi_B$ and $\phi_T$ respectively, due to constant velocity motion. The Doppler PRF is also assumed to be high enough so that $$|\phi_B|, |\phi_T| < \pi/2$$

The electronic noise of the ultrasound signal path due to electrical and thermal effects is assumed to be uncorrelated from echo to echo, with a power spectral density, $\epsilon = dP_N/d\phi$, independent of phase shift angle, $\phi$. The expected value of the power of the filtered linear and nonlinear signals can be expressed as:

$$E\{P_l\} = H_l(\phi_B)^2 \cdot B_{nl} + H_l(\phi_B + \pi)^2 \cdot B_l + H_l(\phi_T + \pi)^2 \cdot T_l +$$
$$\varepsilon \cdot \frac{1}{2\pi} \int_{-\pi}^{\pi} H_l(\phi)^2 \, d\phi$$
$$= E\{P_{B,l}\} + E\{P_{T,l}\} + E\{P_{N,l}\}$$

and $$E\{P_{nl}\} = H_{nl}(\phi_B)^2 \cdot B_{nl} + H_{nl}(\phi_B + \pi)^2 \cdot B_l + H_{nl}(\phi_T + \pi)^2 \cdot T_l +$$
$$\varepsilon \cdot \frac{1}{2\pi} \int_{-\pi}^{\pi} H_{nl}(\phi)^2 \, d\phi$$
$$= E\{P_{B,nl}\} + E\{P_{T,nl}\} + E\{P_{N,nl}\}$$

where $P_{B,l}$, $P_{T,l}$ and $P_{N,l}$ denote components of the high-pass filtered signal due to microbubbles, tissue and noise respectively, and $P_{B,nl}$, $P_{T,nl}$ and $P_{N,nl}$ denote corresponding components of the low-pass filtered signal. The expression E{•} denotes expected value.

To segment data for contrast imaging, it must be decided whether or not a sample volume contains microbubbles based on the values of $P_l$ and $P_{nl}$, and display colour or grayscale data accordingly. Two separate extremes exist: noise-limited imaging and tissue-limited imaging.

Noise-Limited Imaging:

When the echoes from tissue are weak enough to be suppressed by the Doppler lowpass filter, $E\{P_{T,nl}\}$ may be neglected in the preceding equation. We then have $$E\{P_{nl}\} = E\{P_{N,nl}\}$$

if microbubbles are not present in the sample volume, and $$E\{P_{nl}\} = E\{P_{B,nl}\} + E\{P_{N,nl}\}$$

if microbubbles are present in the sample volume. A simple power threshold, $P_{TH}$, set above the noise level, may be used to segment microbubble and tissue echoes:

$$P_{nl} > P_{TH}? \quad \{\text{True: microbubbles; False: tissue}\}$$

The threshold, $P_{TH}$, should be set so that it is higher than the level of random noise in the baseline image.

Tissue-Limited Imaging:

When the echoes from tissue are much larger than the background noise, the noise terms may be neglected in the preceding equations. Consider the ratio, $\rho$, of the nonlinear signal power divided by the linear signal power:

$$\rho = P_{nl}/P_l$$

When the sample volume contains tissue alone, $$\rho = \frac{P_{T,nl}}{P_{T,l}} = \frac{H_{nl}(\phi_T + \pi)^2}{H_l(\phi_T + \pi)^2} = k(\phi_T)$$

where $k(\phi_T)$ is a function of tissue velocity whose properties are determined by the properties of the low-pass and high-pass filters. For stochastic scattering from tissue, ultrasound speckle may cause decorrelation between $P_{T,nl}$ and $P_{T,l}$, which will increase the variance of $\rho$. However, the strong linear tissue echoes that contribute to $P_{T,nl}$ commonly result from specular reflection, and are less affected by speckle.

When the sample volume contains microbubbles and tissue, the nonlinear signal power, $P_{nl}$, will increase relative to the linear signal power, $P_l$, and $\rho$ will increase accordingly. Under these conditions, a new decision criterion may be used:

$$\rho > \rho_{TH}? \quad \{\text{True: microbubbles; False: tissue}\}$$

The threshold, $\rho_{TH}$, should be set so that it is higher than $\rho$ for the strongest tissue echo components present in the image.

The two thresholds discussed above may be combined into a single decision criterion:

$$P_{nl} > \rho_{TH} \cdot P_l + P_{TH}? \quad \{\text{True: microbubbles; False: tissue}\}$$

The right hand side of this inequality may be viewed as an estimate of the contributions to the nonlinear signal, $P_{nl}$, due to tissue and noise. If the measured value of $P_{nl}$ exceeds this threshold, then we may conclude that significant nonlinear scattering has occurred and that microbubbles are present in the sample volume. Although, for simplicity, this analysis assumes negligible nonlinear scattering from tissue, these techniques will also perform well in the presence of tissue nonlinearities, provided that the ratio of nonlinear to linear scattering from bubbles is significantly higher than that from tissue, which is generally the case. The nonlinear harmonic echoes from tissue are the result of nonlinear propagation of the transmitted sound followed by linear scattering from tissue. Thus, the nonlinear echo components of $P_{nl}$ arising from tissue will be directly proportional to the strength of the corresponding linear echo components of $P_l$. The factor $\rho$ can thus be chosen or adjusted to compensate for both the linear and nonlinear tissue components of $P_{nl}$. For tissue imaging without contrast media, this same processor can be used to determine whether or not a given echo signal is likely to have been caused by nonlinear tissue echoes or predominantly linear clutter and noise.

Figure 5:
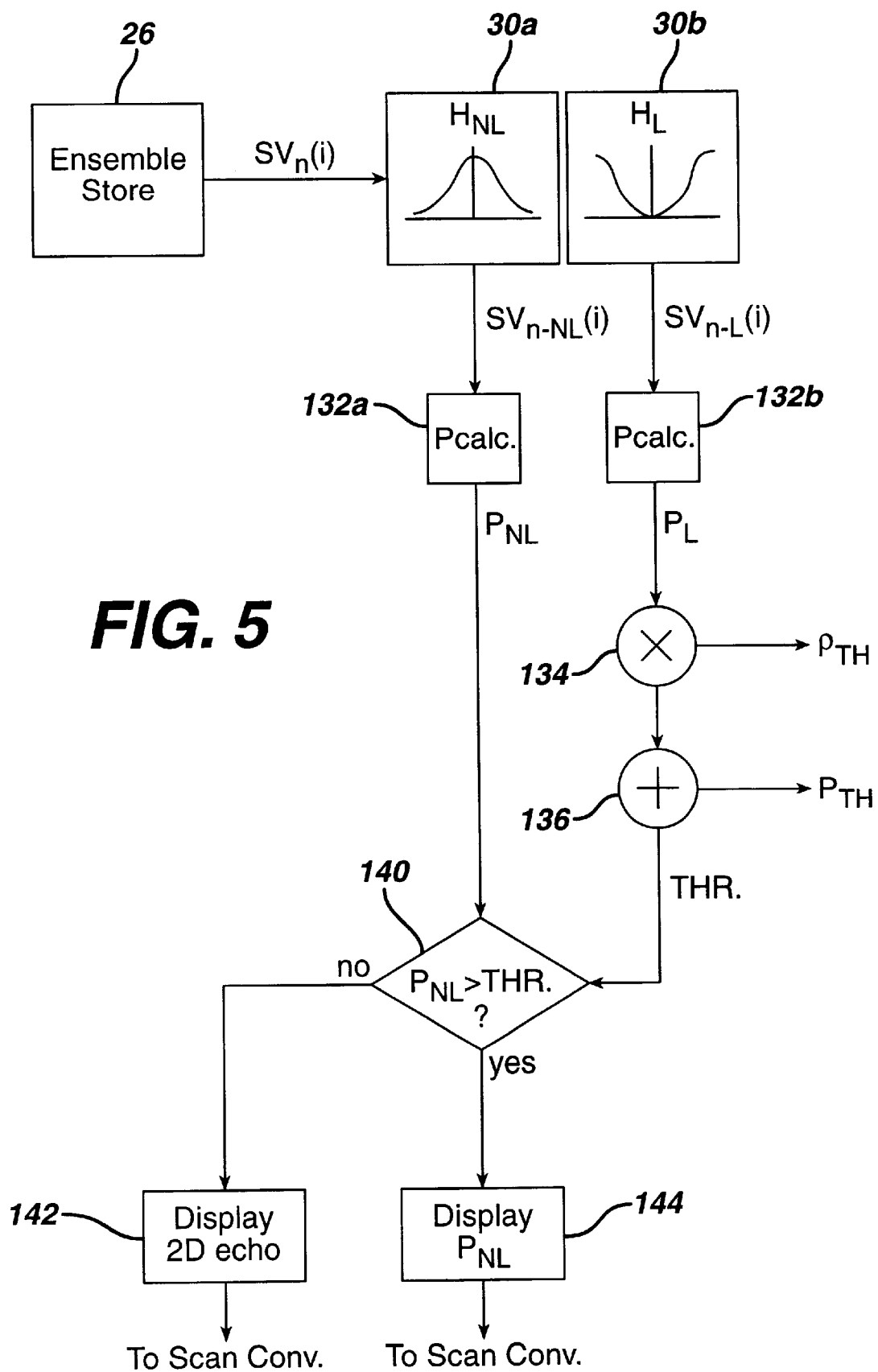
FIG. 5 illustrates in block diagram form the details of apparatus which performs segmentation in accordance with the principles of the present invention.

Referring now to FIG. 5, a first embodiment for performing this segmentation is shown in block diagram form. The output of the ensemble store 26 is coupled to the matrix wall filter 30, which in this embodiment is constructed as two filters 30a and 30b providing two filter characteristics, $H_{NL}$ and $H_L$. In this example the ensemble of echo data acquired from a particular sample volume $SV_n$ is composed of i samples, where i is two or greater. The echo data is filtered by the two filter characteristics $H_{NL}$ and $H_L$ to produce filtered nonlinear and linear output data of the form $SV_{n\text{-}NL}$(i) and $SV_{n\text{-}L}$(i). The echo signal power of the nonlinear and linear passbands, $P_{NL}$ and $P_L$ is estimated by power calculating circuits 132a and 132b which compute the signal power of the filtered linear and nonlinear signal data by the expression $\sqrt{I^2 + Q^2}$.

The right-hand side of the preceding inequality is formed by multiplying the linear power component $P_L$ by the ratio value $\rho_{TH}$ in multiplier 134, and adding the noise power threshold $P_{TH}$ to this product in adder 136. In a constructed embodiment of the present invention the value $\rho_{TH}$ may be set by the user or set automatically or adaptively by the ultrasound system. As mentioned previously, $\rho_{TH}$ is a value based upon the expected ratio of the nonlinear signal to the linear signal for the case where the echo signal is coming from tissue in the absence of any contrast agent. For example the ultrasound system may have a user gain control by which the user controls the amount of color artifacts from specular or highly echogenic reflectors in the baseline image. The value set by this user control may be used to produce the $\rho_{TH}$ value. The value used for $\rho_{TH}$ may be one which is proportional to the expected ratio of $P_{nl}$ to $P_l$ for tissue, for example. Alternatively, the ultrasound system setup may have a default value for $\rho_{TH}$, which may be used directly or subject to user adjustment. As another alternative, the baseline images may be sampled, preferably where specular reflectors are present, and the results used to adaptively compute a value for $\rho_{TH}$. Since this value is a ratio of expected or calculated nonlinear/linear signal power, in many cases the value will, as mentioned above, exhibit some velocity dependence. It may also exhibit variations due to image speckle, and may vary somewhat with depth if weakly nonlinear tissue components are present.

The value used for $P_{TH}$ may be a preset, measured, or estimated threshold chosen relative to the measured or predicted electronic noise levels of the system. As is well known in the art, ultrasound signal noise levels are generally depth-dependent, although a fixed threshold level may also be used in an embodiment of the present invention.

The sum of these two factors produced at the output of summing circuit 136 is termed THR. in FIG. 5. This value is compared with the nonlinear echo signal power level $P_{NL}$ in a comparator 140. If the value of $P_{NL}$ for the echo exceeds the value of THR., the echo is determined to have come from a contrast agent, and the "yes" answer causes a command 144 to be issued to the scan converter (or image processor) to use the value of $P_{NL}$, a nonlinear echo value, at this point in the image. Alternatively or additionally, the command may cause the point in the image to be displayed in color, when color is being used to highlight contrast in the image.

If the answer to the comparison is "no," a command 142 is issued to the scan converter or image processor, causing a 2D tissue echo signal to be displayed at the point in the image. This may cause a signal based upon $P_L$, a linear echo value, to be displayed, or the echo produced by B mode processing for that point of the image. If the image being produced is to display the contrast agent in color and tissue in grayscale, this command will cause the point in the image to be displayed in grayscale. If the image being produced is only to depict the contrast agent without tissue, the command 142 may blank the point in the image.

Alternatively, $P_l$ may be scaled by a factor $\rho$ and subtracted from $P_{nl}$ in an effort to suppress the components of $P_{nl}$ resulting from tissue scattering (for contrast imaging), or from tissue clutter (for tissue harmonic imaging). Here, $\rho$ should be chosen such that $\rho \cdot P_{nl}$ is the predicted value of the component of $P_{nl}$ resulting from linear scattering. The result, $P_{nl} - \rho \cdot P_l$, may be compared to a power threshold, $P_{thresh}$, to determine the likelihood that the corrected nonlinear echo signal intensity is not due to electronic noise and to segment the image accordingly. It may also be used as a display parameter in a grayscale or color image. Optionally, an additional factor, $P_{th}$, may be subtracted from the signal to correct for electronic noise.

Figure 6A:
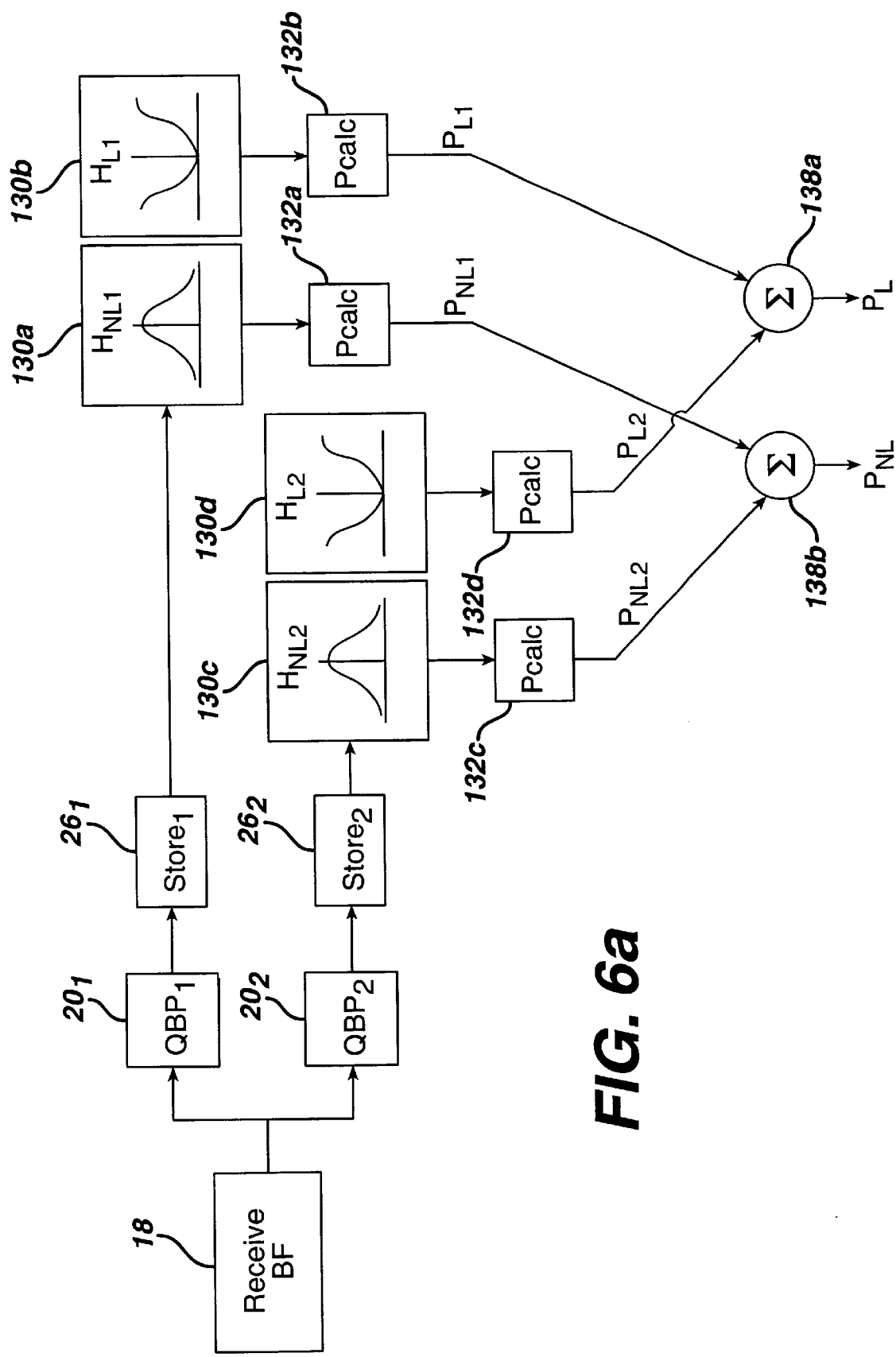
FIG. 6a illustrates another embodiment of the apparatus of FIG. 5 which exploits speckle reduction to further improve the effectiveness of the inventive technique.

Since the linear and nonlinear echo signals may have different speckle characteristics, it is desirable to suppress speckle during the formation of the $P_{nl}$ and $P_l$ signals. One or more speckle suppression techniques including aperture compounding, rf frequency compounding, spatial compounding and Doppler frequency compounding can be applied to one or both of the signal paths to reduce speckle and improve the performance of the inventive technique. Note that the matrix wall filters used in the illustrated embodiments automatically perform some speckle reduction through Doppler frequency compounding provided that the ranks of the matrix filters are greater than one. In FIG. 6a, speckle is reduced by frequency compounding. In this embodiment the echo signals are processed in parallel through two or more separate QBP signal paths 20₁ and 20₂ with different filter, phase and/or frequency response characteristics. The processed data from each signal path is stored in storage devices store₁ 26₁, and store₂ 26₂, then applied to matched pairs of wall filters 130a,130b, and 130c,130d. The $H_{NL}$ and $H_L$ outputs of the wall filters are converted to signal power estimates by signal power calculating circuits 132a–132d, and the corresponding linear and nonlinear echo power signals are added together in summers 138a and 138b to form the speckle-reduced estimates of the nonlinear and linear echo signal power $P_{NL}$ and $P_L$, the speckle reduction being accomplished at this step by combining the different QBP bands of the signal. These parallel paths may be implemented using physically separate hardware paths, or by time sharing the same hardware components.

Figure 6B:
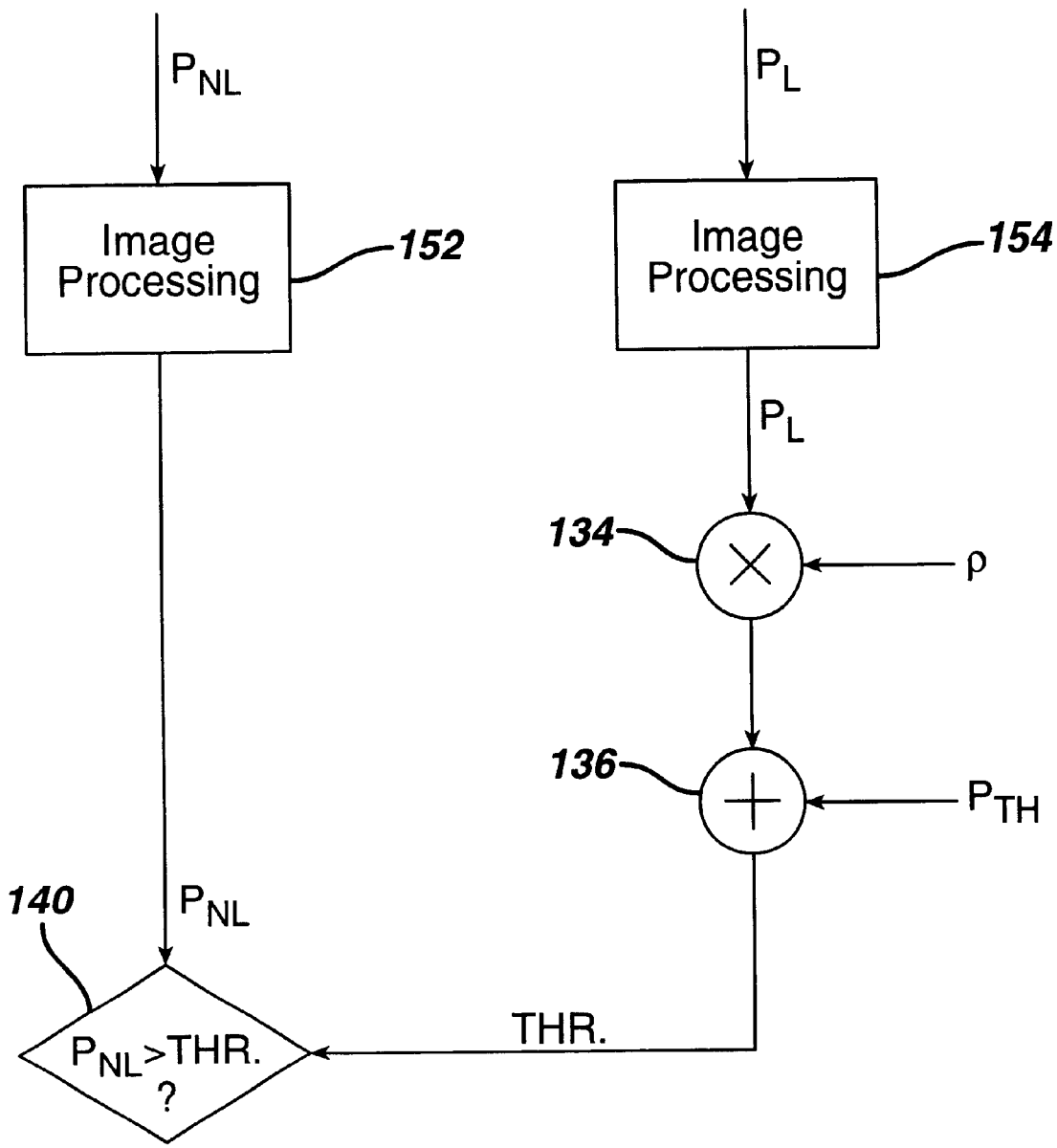
FIG. 6b illustrates an embodiment of the present invention in which speckle is reduced through image processing.

An alternate technique for accomplishing speckle reduction is to use spatial and/or temporal image processing techniques on the pre or post scan converted $P_{NL}$ and $P_L$ signals as shown in FIG. 6b. The image processing circuits 152 and 154 may spatially process the nonlinear and linear signal components by a spatial kernel filter, for example, to reduce speckle. These speckle-reduced power estimates are then used to provide contrast and tissue segmentation as described in FIG. 5. Optionally, two or more of the foregoing speckle reduction techniques may be combined to enhance speckle reduction.

Speckle may be reduced by other techniques besides frequency compounding. For instance, echo signals for a given point in the image may be acquired from different look directions, which may be combined to reduce speckle by spatial compounding as described in U.S. Pat. No. 6,126,599. Speckle may also be reduced by the use of different apertures, as signals using discrete transmit or receive apertures will exhibit different speckle characteristics, which may then be combined to reduce speckle. Another method for reducing speckle is a kernel image processing technique described in U.S. Pat. No. 5,841,889. In the embodiment of FIG. 6a speckle reduction will be accomplished so long as the inputs to the two pairs of wall filters contain data that has been processed differently. Among the processing differences that will suffice are differences in: look direction; receive aperture/beamforming delays, and rf filter response (e.g., center frequency, bandwidth, windowing function).

While the present invention is well adapted to reducing artifacts and improving sensitivity when imaging with contrast agents at low transmit power levels, the principles of the present invention can also be applied to improving tissue harmonic imaging at higher transmit power levels. In tissue harmonic imaging it is nonlinear components developed as the transmit wave passes through the body and contained in the echo signals which are to be detected and used for display. Signals from other causes such as multipath reflections, reverberations and aberration artifacts, which are largely linear in nature, can produce clutter artifacts and are desirably suppressed. The processing described above can be used to suppress electronic noise and clutter artifacts in a grayscale or color tissue harmonic image. The comparison described above, $P_{nl} > \rho_{TH} \cdot P_l + P_{TH}$, can be used with $P_{TH}$ being set adaptively, empirically, or by default from the electronic noise level of the ultrasound system and $\rho_{TH}$ is derived from the measured or anticipated ratio of tissue harmonic to linear clutter signal components. If the answer to the comparison for a given echo signal is "yes," then the harmonic echo signal or a signal related to $P_{NL}$ is displayed. If the answer to the comparison is "no," then the point in the image is blanked or displayed as black (no grayscale). For two-pulse pulse inversion processing both the sum and difference of the rf echoes of the two pulses are computed to separate the nonlinear (second harmonic) and linear (fundamental frequency) components. The separate identity of the components is maintained at least through production of the right-hand comparison inequality term and, if desired, selection of either the linear or nonlinear signal power component.

Figure 7:
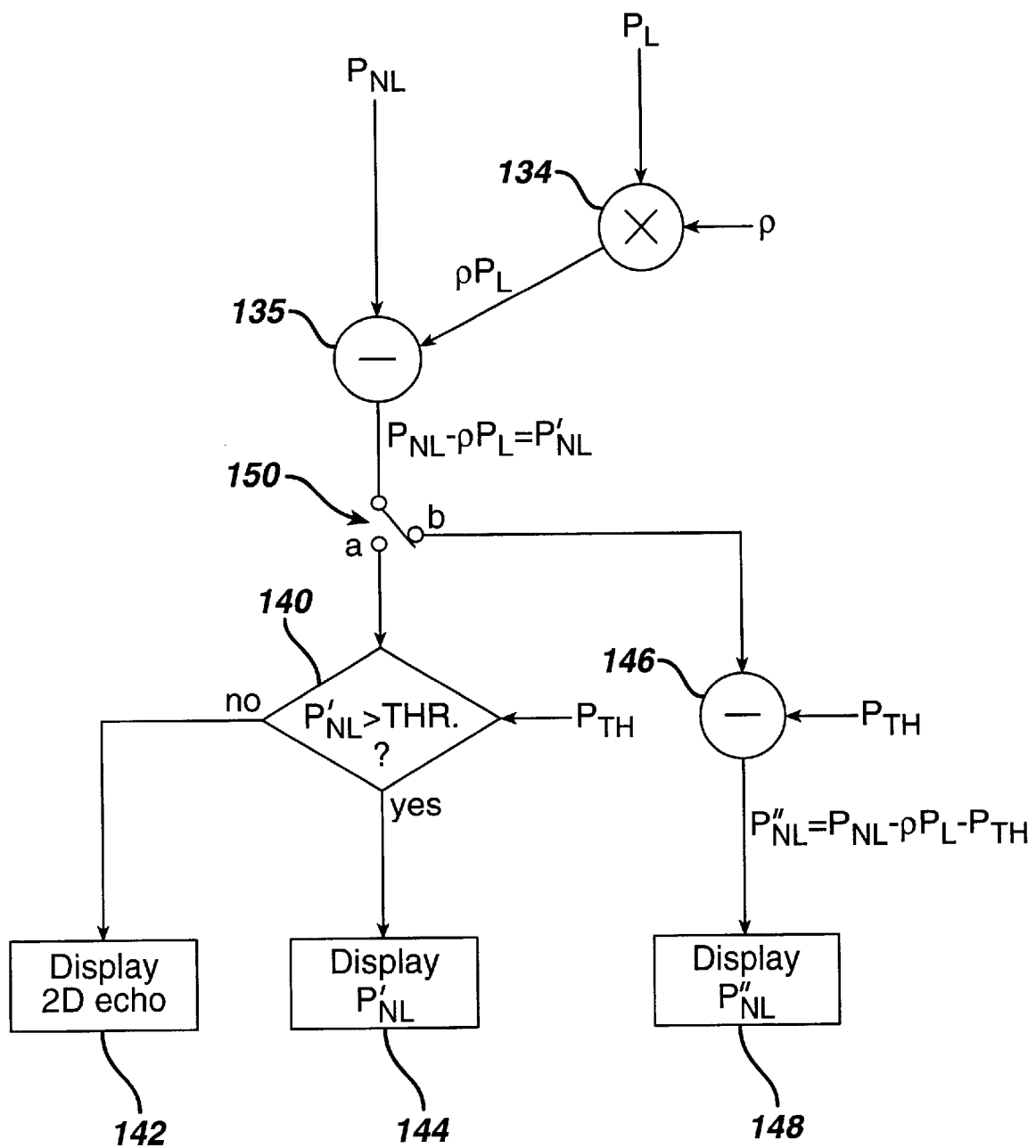
FIG. 7 illustrates a segmentation process which selects from among differently derived nonlinear display signals.

FIG. 7 illustrates a segmentation process which alternatively provides two forms of nonlinear signal components for display. Through multiplier 134, subtractor 135, and comparator 140, with the switch 150 set in the "a" position, either a 2D echo signal is chosen for display at 142 or a nonlinear component $P'_{NL}$ is chosen for display at 144', similar to the processing of $P'_{NL}$ is the nonlinear echo signal power component $P_{NL}$ reduced by a factor $P'_{NL}$ to account for unwanted linear signal leakage into the nonlinear signal spectrum. When the switch 150 is set to the "b" position, the component chosen for display at 148 is a nonlinear signal component $P''_{NL}$ which is equal to the nonlinear power component $P_{NL}$ reduced by both a factor $P'_{NL}$ to account for unwanted linear component contamination and a noise power threshold $P_{TH}$. The noise power threshold $P_{TH}$ may be the same as or different from the noise power threshold used by the comparator 140.

Variation of the illustrated embodiments will readily occur to one skilled in the art. For instance, the ensemble storage and the Doppler filters may be applied directly to the rf echo data prior to QBP filtering and quadrature demodulation, in which case Doppler filtering may be performed with weighted sums of the echo components from each sample volume. For 2-pulse pulse inversion suitable weights would be [+1 +1] for $H_{NL}$ and [+1 −1] for $H_L$. For 3-pulse pulse inversion suitable weights would be [1 2 1] for $H_{NL}$ and [1 −2 1] for $H_L$. For 4-pulse pulse inversion suitable weights would be [1 3 3 1] for $H_{NL}$ and [1 −3 3 −1] for $H_L$. The transmitted beams need not be axially aligned but may be laterally separated, so long as there is a significant degree of acoustic overlap between successive pulses in the Doppler ensemble. If successive samples are acquired in this manner from neighboring lines of sight, the Doppler filtering may be implemented with a laterally sliding FIR filter. Different ensembles may be acquired in an interleaved manner. While the illustrated embodiments use pulse inversion Doppler and Doppler frequency (wall filter) processing to separate linear and nonlinear echo components, the same principles can be applied to phase and amplitude modulated variants of pulse inversion Doppler and to rf harmonic imaging. In the latter case, the "nonlinear" filters should be centered near the second harmonic of the transmission frequency (or another harmonic, ultraharmonic or subharmonic), and the "linear" filters should be centered near the transmit frequency. Similar processing to that described herein may be used for grayscale contrast image (no color) at low transmit power levels.

What is claimed is:

1. An ultrasonic diagnostic imaging system which produces images from linear and nonlinear ultrasonic signal components comprising:
   a transmitter which transmits a series of one or more differently modulated transmit pulses;
   a receiver which receives echo signals in response to the transmit pulses;
   a signal processor, responsive to the received echo signals, which calculates both linear and nonlinear echo signal components;
   a segmentation processor, responsive to both the linear and nonlinear echo signal components, which acts to determine the predominant characteristic of an echo signal on the basis of the relative power of the linear and nonlinear signal components; and
   a display processor, responsive to the segmentation processor, which displays an echo signal on the basis of the determined predominant characteristic.

2. The ultrasonic diagnostic imaging system of claim 1, wherein the transmitter is a pulse inversion or pulse inversion Doppler transmitter.

3. The ultrasonic diagnostic imaging system of claim 1, wherein the signal processor calculates both nonlinear and linear echo signal components using radio frequency filtering, Doppler frequency filtering, or a combination of radio frequency filtering and Doppler frequency filtering.

4. The ultrasonic diagnostic imaging system of claim 1, wherein the segmentation processor acts to compare the nonlinear component of the echo signal to an estimate of contributions to the nonlinear component due to linear and/or weakly nonlinear scattering and noise.

5. The ultrasonic diagnostic imaging system of claim 2, wherein the pulse inversion processor exhibits a first filter characteristic for preferentially passing nonlinear echo signal components relative to linear echo components, and a second filter characteristic for preferentially passing linear echo components relative to nonlinear echo signal components.

6. The ultrasonic diagnostic imaging system of claim 5, wherein the pulse inversion processor comprises a pulse inversion Doppler filter.

7. The ultrasonic diagnostic imaging system of claim 1, further comprising first and second signal power detectors, coupled to the pulse inversion processor, which act to estimate the power of the linear and nonlinear echo signal components.

8. The ultrasonic diagnostic imaging system of claim 7, wherein the segmentation processor is responsive to the linear and nonlinear signal power estimates produced by the signal power detectors.

9. The ultrasonic diagnostic imaging system of claim 1, further comprising a speckle reduction processor, responsive to received echo signals and having an output coupled to the segmentation processor, which acts to reduce the speckle artifact of received echo signals.

10. The ultrasonic diagnostic imaging system of claim 1 wherein the desired signal is a nonlinear echo signal from microbubble contrast agents and the undesired signal is a combined echo signal from tissue and electronic noise.

11. The ultrasonic diagnostic imaging system of claim 1, wherein the desired signal is a nonlinear echo signal from tissue and the undesired signal is a combined electronic noise and linear echo signal from tissue.

12. The ultrasonic diagnostic imaging system of claim 1 wherein the signal processor processes the received echoes with a combination of Doppler and radio frequency wall filters to produce separate signals representative of desired and undesired echo components respectively.

13. The ultrasonic diagnostic imaging system of claim 1 wherein the signal processor processes the received echoes with Doppler wall filters or radio frequency wall filters to produce separate signals representative of desired and undesired echo components respectively.

14. The ultrasonic diagnostic imaging system of claim 1 wherein the transmitter is a pulse inversion Doppler transmitter which transmits a sequence of two or more differentially modulated transmit pulses.

15. The ultrasonic diagnostic imaging system of claim 1 wherein the segmentation processor determines the predominant characteristic of an echo signal on the basis of the comparison:

$$(\text{Desired Signal Power}) \geq \rho(\text{Undesired Signal Power}) + (\text{Constant}).$$

16. The ultrasonic diagnostic imaging system of claim 1 further comprising a compensation processor, responsive to the segmentation processor, which acts to correct the power of a desired signal according to the equation:

(Corrected Power of Desired Signal=(Uncorrected Power of Desired Signal)−ρ(Power of Undesired Signal)−(Constant)

where ρ is a scaling factor.

17. A method for segmenting linear and nonlinear ultrasonic echo signals comprising:
receiving a plurality of echo signals from a target in response to differently modulated transmit signals;
identifying the linear and nonlinear components of the echo signals by pulse inversion processing;
comparing the nonlinear component against a threshold which is a function of an estimate of the contributions to the nonlinear component due to linear and weakly nonlinear scattering and electronic noise; and
identifying at least one of echo signals which exceed the threshold as nonlinear in character and echo signals which do not exceed the threshold as linear in character.

18. The method of claim 17, wherein identifying further comprises determining an echo signal to have originated from a contrast agent or a combination of tissue and electronic noise.

19. The method of claim 17, wherein identifying comprises displaying an echo signal identified as nonlinear in a distinguishing manner in an ultrasonic image display.

20. The method of claim 19, wherein identifying comprises displaying an echo signal identified as nonlinear in a distinguishing color in an ultrasonic image display.

21. The method of claim 17, wherein identifying comprises displaying an echo signal identified as linear in a distinguishing manner in an ultrasonic image display.

22. The method of claim 21, wherein identifying comprises displaying an echo signal identified as linear in grayscale in an ultrasonic image display.

23. The method of claim 17, further comprising transmitting a plurality of axially aligned, differently modulated transmit signals to the target.

24. The method of claim 17, further comprising transmitting a plurality of laterally adjacent, differently modulated transmit signals to the target.

25. A method for segmenting linear and nonlinear ultrasonic echo signals comprising:
receiving an echo signal which may contain linear and nonlinear signal components from a target in response to a transmit signal;
processing the echo signal to reduce speckle artifact;
identifying at least one of the linear and nonlinear components of the echo signal;
estimating the contributions to the echo signal due to linear and weakly nonlinear scattering and electronic noise; and
identifying the echo signal as originating from a predominately linear or nonlinear reflector on the basis of the estimate.

26. The method of claim 25, wherein identifying comprises filtering the echo signal by a first filter having a passband which passes predominantly linear signal components, and by a second filter having a passband which passes predominantly nonlinear signal components.

27. The method of claim 26, wherein identifying further comprises filtering the echo signal by a third filter having a passband which passes linear signal components, and by a fourth filter having a passband which passes nonlinear signal components;
wherein the echo signals received by the first and second filters have been differently processed than the echo signals received by the third and fourth filters; and
wherein processing the echo signal to reduce speckle artifact comprises combining signals produced by the filters.

28. The method of claim 25, wherein processing the echo signal to reduce speckle artifact comprises at least one of the processes of frequency compounding, spatial compounding, processing signals produced by different transmit or receive apertures, and kernel image processing.

29. The method of claim 25, further comprising transmitting, for each echo signal, a plurality of differently modulated transmit signals 30. The method of claim 29, wherein the transmit signals are differently modulated by at least one of phase, polarity, or amplitude.

31. A method for segmenting linear and nonlinear ultrasonic echo signals comprising:
receiving an echo signal which may contain linear signal components and nonlinear tissue harmonic signal components from a target in response to a transmit signal;
identifying at least one of the linear signal clutter and nonlinear tissue harmonic components of the echo signal;
estimating the contributions to the echo signal due to clutter and electronic noise; and
identifying tissue harmonic signals for display on the basis of the estimate.

32. The method of claim 31, wherein echo signals which are not identified as tissue harmonic signals are suppressed in the display.

33. The method of claim 31, further comprising transmitting, for each echo signal, a plurality of differently modulated transmit signals 34. The method of claim 33, wherein the transmit signals are differently modulated by at least one of phase, polarity, or amplitude.

35. A method for displaying nonlinear ultrasonic echo information comprising:
receiving an echo signal from a target which may contain linear and nonlinear signal components;
separating the predominantly linear and predominantly nonlinear components of the echo signal;
scaling the linear component to produce an estimate of the residual linear component of the nonlinear component; and
combining the nonlinear component and the scaled linear component to produce a display signal.

36. The method of claim 35, further comprising transmitting, for each echo signal, a plurality of differently modulated transmit signals 37. The method of claim 36 wherein separating comprises separating the linear and nonlinear components by pulse inversion processing.

38. The method of claim 17, wherein identifying further comprises determining an echo signal to have originated from tissue harmonics or a combination of clutter artifacts and electronic noise.

* * * * *